United States Patent [19]

George et al.

[11] Patent Number: 5,244,894

[45] Date of Patent: Sep. 14, 1993

[54] 2-AMINOPYRIMIDINE-4-CARBOXAMIDE DERIVATIVES, THEIR PREPARATION AND THEIR USE IN THERAPEUTICS

[75] Inventors: Pascal George, St. Arnoult en Yvelines; Philippe Manoury, Verrieres le Buisson; Benoit Marabout, Massy; Jacques Froissant, Moree; Jean-Pierre Merly, Sceaux, all of France

[73] Assignee: Synthelabo, Paris

[21] Appl. No.: 904,060

[22] Filed: Jun. 26, 1992

[30] Foreign Application Priority Data

Jun. 27, 1991 [FR] France .................. 91 07939

[51] Int. Cl.⁵ ................ C07D 401/12; A61K 31/505
[52] U.S. Cl. ..................... 514/252; 544/295
[58] Field of Search .................. 544/295; 514/252

[56] References Cited

FOREIGN PATENT DOCUMENTS 2143730 8/1973 Fed. Rep. of Germany .

Primary Examiner—John M. Ford
Attorney, Agent, or Firm—Jacobson, Price, Holman & Stern

[57] ABSTRACT

Compounds corresponding to the general formula (I)

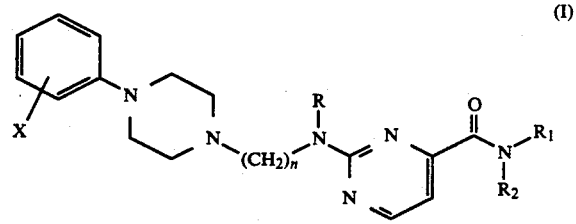

in which n=2 or 3, X=H, F, Cl or OCH$_3$, R=H or CH$_3$, R$_1$=H or CH$_3$, R$_2$=alkyl, hydroxyalkyl, (hydroxy)(methoxy)alkyl, dimethoxyalkyl, 2-(aminosulphonyl)ethyl, 2-(methylsulphonyl)ethyl, 2-(methylsulphonylamino)ethyl, aminocarbonylmethyl which is optionally substituted by nitrogen, phenylethyl which is optionally substituted, pyrimidinylaminoalkyl or arylcaronylaminoalkyl, or else R$_1$ and R$_2$ form, with the nitrogen which carries them, a piperidine, morpholine, thiomorpholine or piperazine ring, optionally substituted by nitrogen. Use in therapeutics.

7 Claims, No Drawings

2-AMINOPYRIMIDINE-4-CARBOXAMIDE DERIVATIVES, THEIR PREPARATION AND THEIR USE IN THERAPEUTICS

The invention relates to 2-aminopyrimidine-4-carboxamide derivatives, their preparation and their use in therapeutics.

SUMMARY OF THE INVENTION

The invention provides a compound which is a 2-aminopyrimidine-4-carboxamide derivative represented by formula (I)

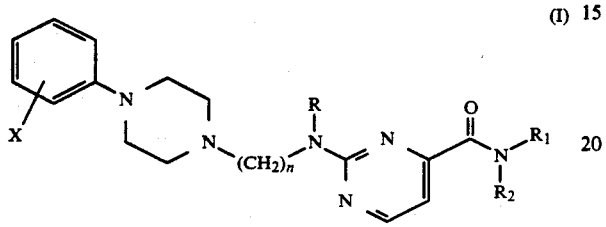
(I)

in which
n represents 2 or 3,
X represents hydrogen, fluorine, chlorine or methoxy, with the proviso that more than one substituent X may be present in which case each X may be the same or different,
R represents hydrogen or methyl,
$R_1$ represents hydrogen or methyl,
$R_2$ represents
  $C_1$-$C_6$ alkyl
  $C_2$-$C_3$ hydroxyalkyl,
  (hydroxy)(methoxy)($C_2$-$C_3$ alkyl),
  dimethoxy($C_2$-$C_3$ alkyl),
  2-(aminosulphonyl)ethyl,
  2-(methylsulphonyl)ethyl,
  2-(methylsulphonylamino)ethyl,
  a group of formula —$CH_2$—CO—$NY_1Y_2$ in which $Y_1$ and $Y_2$, which may be the same or different, each represent hydrogen or $C_1$-$C_6$ alkyl,
  a group of formula —$(CH_2)_2$—Ar in which Ar represents phenyl, optionally substituted by one or more methoxy or aminosulphonyl groups,
  a group of formula

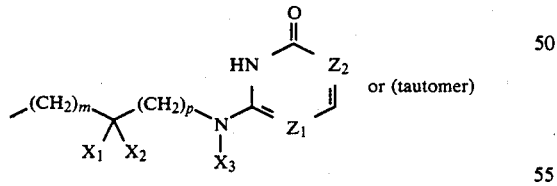

in which m represents 0 or 1, p represents 1 or 2, one of $Z_1$ and $Z_2$ represents —CH— and the other represents a nitrogen atom, and either $X_1$, $X_2$ and $X_3$ each represent hydrogen or $X_1$ and $X_2$ each represent methyl and $X_3$ represents hydrogen or $X_1$ represents hydrogen and $X_2$ and $X_3$ together form a chain of formula —$(CH_2)_{4-p}$ in which p is as defined above, or
a group of formula

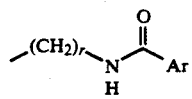

in which r represents 2 or 3 and Ar represents phenyl optionally substituted by one or more chloro, methoxy or amino groups, or 2-furanyl or 2-tetrahydrofuranyl or 3-pyridinyl, or $R_1$ and $R_2$ form, together with the nitrogen atom to which they are attached,
a group of formula

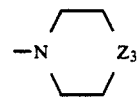

in which $Z_3$ represents oxygen, sulphur, sulphonyl or a group of formula N—$R_4$ in which $R_4$ represents hydrogen, methyl, acetyl, tert-butyloxycarbonyl, phenyloxycarbonyl or a group of formula

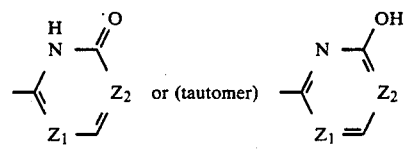

in which $Z_1$ and $Z_2$ are as defined above, or
a group of formula

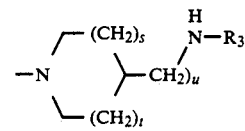

in which either s represents 0 and t represents 2, or both s and t represent 1, u represents 0 or 1 and $R_3$ represents hydrogen, tert-butyloxycarbonyl, benzyloxycarbonyl or a group of formula

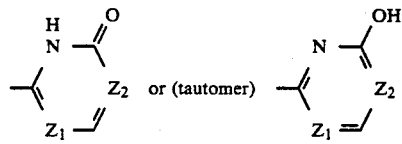

in which $Z_1$ and $Z_2$ are as defined above; or
a pharmaceutically acceptable acid addition salt thereof.

Compounds of the invention are suitable for use as active therapeutic substances, particularly for use as $\alpha_1$-adrenergic receptor antagonists.

DETAILED DESCRIPTION OF THE INVENTION

Compounds of formula (I) preferably contain one or two substituents X. When one substituent X is present, it is preferably at the 3-position. When two substituents X are present, they are preferably at the 2- and 5-positions, and most preferably methoxy is a the 2-position and chloro is at the 5-position.

In accordance with the invention, the compounds of general formula (I) can be prepared according to a process illustrated by the Scheme below. Compounds of formula (I) may be converted into salts thereof in a manner known per se.

An amide of general formula (II), in which n, X and R are as defined above, is converted to an ester of general formula (III) in which R' represents a $C_1$–$C_4$ alkyl group by reaction with an aliphatic alcohol, for example methanol, in the presence of an acid, for example gaseous hydrochloric acid, at a temperature of 0° to 60° C., and the ester thus obtained is then reacted with an amine of general formula (IV), in which $R_1$ and $R_2$ are as defined above.

When the amine of general formula (IV) is primary ($R_1$=H), the reaction is carried out in an aliphatic alcohol, for example methanol or n-butanol, at a temperature of 0° to 100° C.

When the amine of general formula (IV) is secondary ($R_1$=CH$_3$), the corresponding dimethylaluminium amide is prepared beforehand by means of trimethylaluminium, in an inert solvent such as hexane, toluene or dichloromethane, and it is the amide thus obtained which is reacted with the ester of general formula (III) in dichloromethane at a temperature of 0° to 40° C.

Scheme

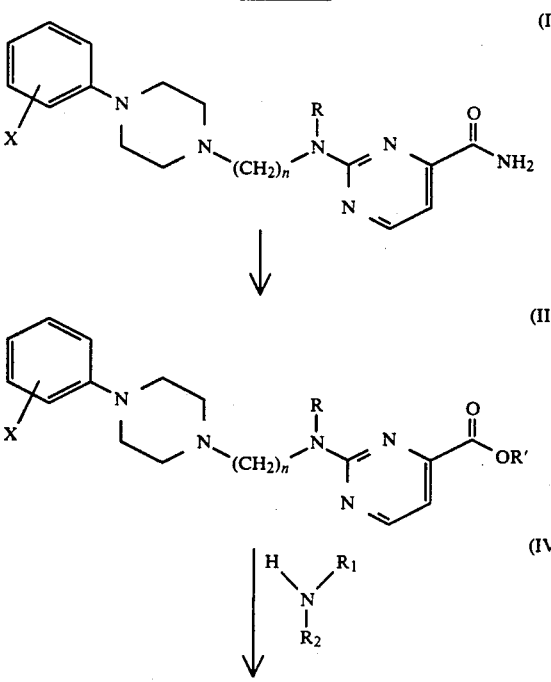

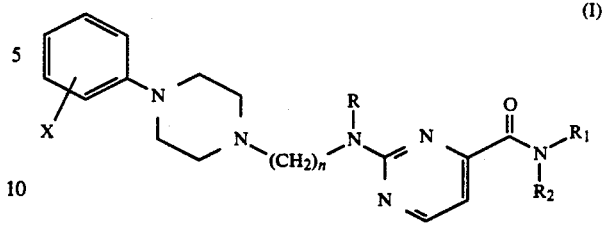

The starting compounds of general formula (II) can be prepared by methods analogous to those described in Patent Application EP-0435749.

The amines of general formula (IV) in which $R_1$ represents a hydrogen atom and $R_2$ represents a group of general formula

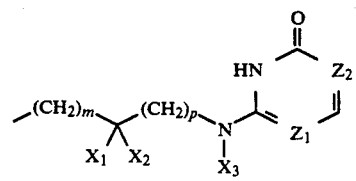

can be prepared by analogous methods to those described in Biochem. Biophys. Res. Comm. (1990) 170(1), 243 and in Patent Application EP-0373891.

The amines of general formula (IV) in which $R_1$ represents a hydrogen atom and $R_2$ represents a group of general formula

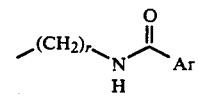

can be prepared by analogous methods to the methods mentioned above.

The amines of general formula (IV) in which $R_1$ represents a hydrogen atom and $R_2$ represents a group of general formula —CH$_2$—CO—NY$_1$Y$_2$ can be prepared by methods analogous to those described in Patent Applications EP-0062161, EP-0227410 and EP-0316179.

Finally, in the case of the amines of general formula (IV) in which $R_1$ and $R_2$ together represent a group of general formula

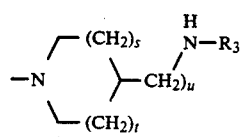

such a protected diamine is used, in the formula of which $R_3$ represents a protecting group such as a benzyloxycarbonyl or a tert-butyloxycarbonyl group. Such protected diamines can be prepared by methods analogous to those described with regard to the synthesis of 1,1-dimethylethyl piperidine-4-carbamate in Patent Applications DE-2831431, EP-0410278 and EP-0417698. If desired, the compound obtained is deprotected according to a known method, for example by trifluoroacetic acid in dichloromethane (in the case of a tert-butyloxycarbonyl group), in order to obtain a compound in the formula of which $R_3$ represents hydrogen and, if desired, the latter is reacted with 2,3-dihydro-4-thioxopyrimidin-2(1H)-one or 2-methylthiopyrimidin-4(1H)-one according to a method analogous to that described in Patent Application EP-0373891.

It is obvious that the various modifications which have been described with regard to the protected amine of general formula (IV) can be carried out directly on the said amine, as described above, but also on the compound of general formula (I), after the reaction of the protected amine of general formula (IV) with the ester of general formula (III).

The following examples illustrate the preparation of some compounds according to the invention.

Elemental microanalyses and IR and NMR spectra confirm the structures of the products obtained.

The compound numbers shown between parentheses in the headings of the examples correspond to those of the table given later.

EXAMPLE 1

Compound No. 1

2-[[3-[4-(3-Chlorophenyl)piperazin-1-yl]propyl]amino]-N-methylpyrimidine-4-carboxamide, hydrochloride.

1.1. Methyl 2-[[3-[4-(3-chlorophenyl)piperazin-1-yl]propyl]amino]-pyrimidine-4-carboxylate 20.76 g (55.4 mmols) of 2-[[3-[4-(3-chlorophenyl)piperazin-1-yl]propyl]amino]pyrimidine-4-carboxamide and 600 ml of methanol are introduced into a 1 l, round bottomed flask, a stream of gaseous hydrochloric acid is then passed in for a few minutes and the mixture is heated, at the reflux temperature of the methanol, for 1.5 hour.

The solvent is evaporated under reduced pressure, 200 ml of dichloromethane are added to the residue and the mixture is cooled to 0° C. The mixture is alkalinised with a saturated aqueous sodium hydrogen carbonate solution, the layers are separated and the organic phase is dried over sodium sulphate, filtered and the solvent evaporated under reduced pressure.

After chromatography on a silica column (eluent: ethyl acetate/methanol mixture, 100/0 to 95/5) and then recrystallisation from cyclohexane, 16.16 g (41.5 mmols) of compound are isolated.

Melting point: 100.5°–101° C.

1.2. 2-[[3-[4-(3-Chlorophenyl)piperazin-1-yl]propyl]amino]-N-methylpyrimidine-4-carboxamide, hydrochloride 4.5 g (11.5 mmols) of methyl 2-[[3-[4-(3-chlorophenyl)piperazin-1-yl]propyl]amino]pyrimidine-4-carboxylate and 200 ml of methanol are introduced into a 0.5 l, round bottomed flask and then the solution is saturated with gaseous methylamine. The reaction mixture is stirred at room temperature while saturating several times with gaseous methylamine. The solvent is evaporated under reduced pressure. 4.05 g (10.4 mmols) of base are obtained to which 104 ml of 0.1N hydrochloric acid in 2-propanol are added. The solvent is evaporated and the product is recrystallised from 2-butanone. 3.8 g of compound are obtained.

Melting point: 166°–168° C.

EXAMPLE 2

Compound No. 60

2-[[3-[4-(3-Chlorophenyl)piperazin-1-yl]propyl]amino]-N,N-dimethylpyrimidine-4-carboxamide, dihydrochloride 4 g (10.2 mmols) of methyl 2-[[3-[4-(3-chlorophenyl)-piperazin-1-yl]propyl]amino]pyrimidine-4-carboxylate and 200 ml of methanol are introduced into a 0.5 l, round bottomed flask and then the solution is saturated with gaseous dimethylamine. The reaction mixture is stirred for three days at room temperature while saturating several times with gaseous dimethylamine. The solvent is evaporated under reduced pressure and, after chromatography on silica (eluent: 100/0 to 90/10 ethyl acetate/methanol mixture), 2.24 g (5.55 mmols) of the compound are obtained in the base form.

80 ml of 0.1N hydrochloric acid in 2-propanol are added to 1.69 g of base. The solvent is evaporated and the product is recrystallised from acetone. 1.94 g (4.08 mmols) of compound are obtained.

Melting point: 194°–198° C.

EXAMPLE 3

Compound No. 69

1-[2-[[3-[4-(5-Chloro-2-methoxyphenyl)piperazin-1-yl]propyl]amino]-4-pyrimidinylcarbonyl]-4-methylpiperazine, dihydrochloride 3.1 Methyl 2-[[3-[4-(5-chloro-2-methoxyphenyl[piperazin-1-yl]propyl]amino]pyrimidine-4-carboxylate 7.8 g (19.2 mmols) of 2-[[3-[4-(5-chloro-2-methoxyphenyl)piperazin-1-yl]propyl]amino]pyrimidine-4-carboxamide and 300 ml of methanol are introduced into a 0.5 l, round bottomed flask, a stream of gaseous hydrochloric acid is then passed in for a few minutes and the mixture is heated at the reflux temperature of the methanol for 1.75 hours. The solvent is evaporated under reduced pressure, 200 ml of dichloromethane are added to the residue and the mixture is then cooled to 0° C. The mixture is alkalinised with a saturated aqueous sodium hydrogen carbonate solution, the organic phase is dried over sodium sulphate, filtered and the solvent is then evaporated under reduced pressure. After chromatography on a silica column (eluent: dichloromethane/methanol mixture, 100/0 to 90/10) and then recrystallisation from cyclohexane, 5.84 g (13.9 mmols) of ester are isolated.

Melting point: 118.5°–119° C.

3.2 1-[2-[[3-[4-(5-Chloro-2-methoxyphenyl)piperazin-1-yl)propyl]amino]-4-pyrimidinylcarbonyl]-4-methylpiperazine, dihydrochloride 80 ml of dichloromethane, 6.8 g of a 25% solution of trimethylaluminium in hexane (23.6 mmols) and then 2.96 g (29.5 mmols) of 1-methylpiperazine in 10 ml of dichloromethane are introduced successively into a 0.25 l, round bottomed flask. The reaction mixture is stirred for 30 minutes at room temperature and 1.84 g (4.72 mmols) of methyl 2-[[3-[4-(5-chloro-2-methoxyphenyl]-piperazin-1-yl]propyl]amino]pyrimidine-4-carboxylate in 10 ml of dichloromethane are then slowly added. The reaction mixture is stirred for 30 minutes at room temperature and then for 3.5 hours at the reflux temperature.

The reaction mixture is cooled to 0° C. with a water-/salt/ice mixture, the reaction mixture is hydrolysed by a few ml of water, left stirring for 1 hour at room temperature, filtered, water is added and the mixture is extracted with dichloromethane (3×150 ml). The solvent is evaporated under reduced pressure and the oil obtained is chromatographed on a silica gel column (eluent: dichloromethane/methanol mixture, 100/0 to 80/20) in order to obtain 1.29 g of base.

56 ml of 0.1N hydrochloric acid in 2-propanol are added to the base in solution in 10 ml of dichloromethane, the mixture is evaporated under reduced pressure and the residue is recrystallised from acetone. 1 g (1.88 mmols) of dihydrochloride is obtained.

Melting point: 253°–256° C.

EXAMPLE 4

Compound No. 30

2-[[3-[4-(5-Fluoro-2-methoxyphenyl)piperazin-1-yl]propyl]amino]-N-[3-[2-oxo-1,2-dihydropyrimidin-4-yl)amino]propyl]pyrimidine-4-carboxamide

4.1. Methyl 2-[[3-[4-(5-fluoro-2-methoxyphenyl)piperazin-1-yl]propyl]amino]pyrimidine-4-carboxylate 3.0 g (7.72 mmols) of 2-[[3-[4-(5-fluoro-2-methoxyphenyl)piperazin-1-yl]propyl]amino]pyrimidine-4-carboxamide and 250 ml of methanol are introduced into a 0.5 l, round bottomed flask, a stream of gaseous hydrochloric acid is then passed in for a few minutes and the mixture is heated at the reflux temperature of the methanol for 1.5 hours. The solvent is evaporated under reduced pressure, 150 ml of dichloromethane are added to the residue and the mixture is then cooled to 0° C. The mixture is alkalinised with a saturated aqueous sodium hydrogen carbonate solution, the organic phase is separated, then dried over sodium sulphate, and filtered and the solvent then evaporated under reduced pressure.

After chromatography on a silica column (eluent: dichloromethane/methanol mixture, 99/1 to 95/5) and then recrystallisation from cyclohexane, 2.6 g (6.44 mmols) of ester are isolated.

Melting point: 102°–103° C.

4.2 2-[[3-[4-(5-Fluoro-2-methoxyphenyl)piperazin-1-yl]propyl]amino]-N-[3-[2-oxo-1,2-dihydropyrimidin-4-yl)amino]propyl]pyrimidine-4-carboxamide 1 g (2.48 mmols) of methyl 2-[[3-[4-(5-fluoro-2-methoxyphenyl)piperazin-1-yl]propyl]amino]pyrimidine-4-carboxylate and 0.55 g (3.27 mmols) of 4-[(3-aminopropyl)amino]pyrimidin-2(1H)-one in 15 ml of 2-propanol are introduced into a 0.1 l, round bottomed flask and the mixture is heated at the reflux temperature of the solvent for 14 hours.

The product precipitates in the reaction mixture; it is collected by filtration and then recrystallised from a mixture of dichloromethane and methanol 0.74 g (1.37 mmols) of white solid is obtained.

Melting point 219°–221° C.

EXAMPLE 5

Compound No. 23

2-[[3-(4-(5-Chloro-2-methoxyphenyl)piperazin-1-yl]propyl]amino]-N-[2-[(4-oxo-1,4-dihydropyrimidin-2-yl)amino]ethyl]pyrimidine-4-carboxamide 1.89 g of (4.5 mmols) of methyl 2-[[3-[4-(5-chloro-2-methoxyphenyl)piperazin-1-yl]propyl]amino]-pyrimidine-4-carboxylate and 0.77 g (5 mmols) of 2-[(2-aminoethyl)amino]pyrimidin-4(1H)-one in 5 ml of n-butanol are introduced into a 25 ml, round bottomed flask. The mixture is heated at the reflux temperature of the solvent for 15 hours and then the solvent is evaporated under reduced pressure.

The crude product is purified by chromatography on a silica gel column (eluent: dichloromethane/methanol mixture, 95/5 to 80/20) and the product obtained is then recrystallised from a mixture of dichloromethane and ethyl acetate in order to obtain 1.04 g (1.92 mmols) of white solid.

Melting point: 118°–120° C.

EXAMPLE 6

Compound No. 35

2-[[2-[4-(5-Chloro-2-methoxyphenyl)piperazin-1-yl)ethyl]amino]-N-[3-[(4-oxo-1,4-dihydropyrimidin-2-yl)amino]propyl]pyrimidine-4-carboxamide

6.1. Methyl 2-[2-[4-(5-chloro-2-methoxyphenyl)piperazin-1-yl]ethyl]amino]pyrimidine-4-carboxylate 6.6 g (16.88 mmols) of 2-[[2-[4-(5-chloro-2-methoxyphenyl)piperazin-1-yl]ethyl]amino]pyrimidine-4-carboxamide and 600 ml of methanol are introduced into a 1 liter, round bottomed flask, a stream of gaseous hydrochloric acid is then passed in for a few minutes and the mixture is heated at the reflux temperature of the methanol for 3 hours. The solvent is evaporated under reduced pressure, 100 ml of dichloromethane are added to the residue and the mixture is then cooled to 0° C. The mixture is alkalinised with a saturated aqueous sodium hydrogen carbonate solution, the organic phase is separated, dried over magnesium sulphate, filtered and then the solvent is evaporated under reduced pressure.

After chromatography on a silica gel column (dichloromethane/methanol eluent, 100/0 to 95/5) and then recrystallisation from cyclohexane, 4.5 g (11.09 mmols) of ester are isolated.

Melting point: 127°–129° C.

6.2. 2-[[2-[4-(5-Chloro-2-methoxyphenyl)piperazin-1-yl)ethyl]amino]-N-[3-[(4-oxo-1,4-dihydropyrimidin-2-yl)amino]propyl]pyrimidine-4-carboxamide 3.0 g (7.4 mmols) of methyl 2-[[2-[4-(5-chloro-2-methoxyphenyl)piperazin-1-yl]ethyl]amino]-pyrimidine-4-carboxylate and 1.5 g (8.9 mmols) of 2-[(3-aminopropyl)amino]pyrimidin-4(1H)-one in 20 ml of n-butanol are introduced into a 100 ml, round bottomed flask. The mixture is heated at the reflux temperature of the solvent for 20 hours and then the solvent is evaporated under reduced pressure.

The crude product is purified by chromatography on a silica gel column (eluent: dichloromethane/methanol mixture, 98/2 to 80/20) and the product obtained is then recrystallised from a dichloromethane/ethyl acetate mixture in order to obtain 1.7 g (3.14 mmols) of white solid.

Melting point: 100°–102° C.

EXAMPLE 7

Compound No. 79

1,1-Dimethylethyl 1-[2-[[2-[4-(5=chloro-2-methoxyphenyl)piperazin-1-yl]ethyl]amino]-4-pyrimidinylcarbonyl]piperidine-4-carbamate, hydrochloride 150 ml of dichloromethane, 10.1 g of a 25% solution of trimethylaluminium in hexane and then 7.0 g (35 mmols) of 1,1-dimethylethyl (piperidin-4-yl)carbamate in 10 ml of dichloromethane are introduced successively into a 0.5 l, round bottomed flask. The reaction mixture is stirred for 30 minutes at room temperature and then 3.9 g (9.6 mmols) of methyl 2-[[2-[4-(5-chloro-2-methoxyphenyl)piperazin-1-yl]ethyl]amino]pyrimidine-4-carboxylate in 20 ml of dichloromethane are slowly added. The reaction mixture is stirred for 30 minutes at room temperature and for 3 hours at the reflux temperature of the dichloromethane and then the reaction mixture is cooled to 0° C. with a water/salt/ice mixture. The reaction mixture is hydrolysed by a few ml of water, left stirring for 1 hour at room temperature, filtered and the solvents evaporated under reduced pressure. The oil obtained is purified by chromatography on silica gel (eluent: dichloromethane/methanol mixture, 98/2 to 90/10) in order to obtain 4.92 g (8.57 mmols) of base.

82.5 ml of 0.1N hydrochloric acid in 2-propanol are added to the base in solution in 10 ml of dichloromethane, the mixture is evaporated under reduced pressure and the product recrystallised from ethyl acetate. 4.61 g (7.55 mmols) of compound are obtained.

Melting point: 194°–197° C.

EXAMPLE 8

Compound No. 81

1-[2-[[2-[4-(5-Chloro-2-methoxyphenyl)piperazin-1-yl]ethyl]amino]-4-pyrimidinylcarbonyl]piperidin-4-amine 3 g (4.9 mmols) of the hydrochloride of 1,1-dimethylethyl 1-[2-[[2-[4-(5-chloro-2-methoxyphenyl)-piperazin-1-yl]ethyl]amino]-4-pyrimidinylcarbonyl]-piperidine-4-carbamate in solution in 20 ml of water and then, dropwise, 10 ml of concentrated hydrochloric acid are placed in a 0.5 l, round bottomed flask. The mixture is stirred for 5 minutes at room temperature and then cooled to 0° C. with an ice/salt/water mixture. 30% aqueous sodium hydroxide solution is added to the reaction mixture to a pH≧8, the mixture is then extracted with dichloromethane, the extracts are dried over magnesium sulphate, filtered and the solvent evaporated under reduced pressure in order to obtain 2 3 g (4.9 mmols) of amorphous solid.

EXAMPLE 9

Compound No. 85

2-[[1-[2-[[2-[4-(5-Chloro-2-methoxyphenyl)piperazin-1-yl]ethyl]amino]pyrimidin-4-ylcarbonyl]piperidin-4-yl]amino]pyrimidin-4(1H)-one 2.3 g (4.9 mmol) of 1-[2-[[2-[4-(5-chloro-2-methoxyphenyl)piperazin-1-yl]ethyl]amino]pyrimidin-4-ylcarbonyl]piperidin-4-amine, and 0.9 g (6.3 mmols) of 2-methylthiopyrimidin-4(1H)-one in solution in 40 ml of m-xylene are introduced into a 0.5 l, round bottomed flask and the mixture is heated at reflux of the m-xylene for 14 hours. The reaction mixture is cooled to room temperature and the solvent is then evaporated under reduced pressure. The crude product is purified by chromatography on a silica gel column (eluent: dichloromethane/methanol, 98/2 to 85/15) in order to obtain 1.56 g (2.74 mmols) of compound.

Melting point: 114°–117° C.

EXAMPLE 10

Compound No. 59

2-[[2-[4-(5-Chloro-2-methoxyphenyl)piperazin-1-yl]ethyl]amino]-N-[2-[(2-furanylcarbonyl)amino]ethyl]-pyrimidine-4-carboxamide, oxalate 1.22 g (3 mmols) of methyl 2-[[2-[4-(5-chloro-2-methoxyphenyl)piperazin-1-yl]ethyl]amino]pyrimidine-4-carboxylate and 0.7 g (4.5 mmols) of N-(2-furanylcarbonyl)ethanediamine in solution in a 3/1 mixture of 2-propanol/methanol are introduced into a 25 ml, round bottomed flask and the reaction mixture is then heated at reflux for 7.5 hours.

The mixture is cooled to room temperature, the solvents are evaporated under reduced pressure and then the oil obtained is chromatographed on silica gel (eluent: dichloromethane/methanol, 100/0 to 95/5) in order to obtain 1.58 g of base.

The base is dissolved in 50 ml of ethanol and 0.27 g (3 mmols) of oxalic acid are added. The mixture is evaporated under reduced pressure and the residue is then recrystallised from a 2-propanol/ethyl acetate mixture in order to obtain 1.5 g (2.43 mmols) of compound.

Melting point: 128°–132° C.

EXAMPLE 11

Compound No. 17

[[2-[[3-[4-(5-Chloro-2-methoxyphenyl)piperazin-1-yl]propyl]amino]pyrimidin-4-ylcarbonyl]amino]-N-propylacetamide 2.4 g (5.7 mmols) of methyl 2-[[3-[4-(5-chloro-2-methoxyphenyl)piperazin-1-yl]propyl]amino]pyrimidine-4-carboxylate and 2.2 g (14.4 mmols) of N-propylglycinamide hydrochloride in solution in a mixture of 30 ml of 2-propanol and 30 ml of 1,2-dichloroethane are introduced into a 0.1 l, round bottomed flask, 2.1 ml (15 mmols) of triethylamine are then added and the mixture is heated at reflux for 14 hours.

The mixture is cooled to room temperature and 100 ml of dichloromethane and 100 ml of water are added. The organic phase is separated, dried over sodium sulphate and the solvents are evaporated under reduced pressure.

The crude product is purified by chromatography on silica gel (eluent: dichloromethane/methanol, 98/2 to 90/10) and the product is recrystallised from a mixture of dichloromethane and acetonitrile in order to obtain 1.8 g (3.57 mmols) of compound.

Melting point: 143.5°–144.5° C.

The table which follows illustrates the chemical structures and the physical properties of some compounds according to the invention.

TABLE

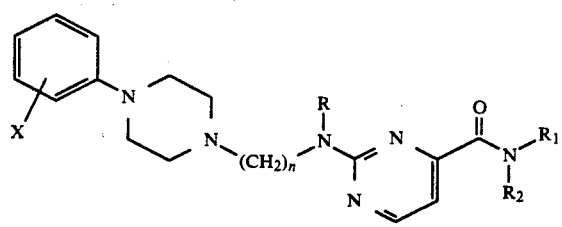

(I)

| N° | X | R | n | —NR₁R₂ | Salt or base | M.p. (°C.) |
|---|---|---|---|---|---|---|
| 1 | 3-Cl | H | 3 | —NH—CH$_3$ | HCl | 166–168 |
| 2 | 2-OCH$_3$, 5-Cl | H | 3 | —NH—CH$_3$ | HCl | 175.5–177.5 |
| 3 | 2-OCH$_3$, 5-Cl | H | 3 | —NH—(CH$_2$)$_2$—CH$_3$ | C$_2$H$_2$O$_4$ | 173.5–175 |
| 4 | 2-OCH$_3$, 5-Cl | H | 3 | —NH—(CH$_2$)$_5$—CH$_3$ | C$_2$H$_2$O$_4$ | 150–151.5 |
| 5 | 2-OCH$_3$, 5-Cl | H | 3 | —NH—(CH$_2$)$_2$—OH | base | 135–136 |
| 6 | 3-Cl | H | 3 | —NH—(CH$_2$)$_3$—OH | C$_2$H$_2$O$_4$ | 157–159 |
| 7 | 2-OCH$_3$, 5-Cl | H | 3 | —NH—(CH$_2$)$_3$—OH | base | 94–95.5 |
| 8 | 2-OCH$_3$, 5-Cl | H | 3 | —NH—CH$_2$—CH(OH)—CH$_2$—OCH$_3$ | base | 124.5–125.5 |
| 9 | 2-OCH$_3$, 5-Cl | H | 3 | —NH—CH$_2$—CH(OCH$_3$)—CH$_2$—OCH$_3$ | C$_2$H$_2$O$_4$ | 148–150 |
| 10 | 3-Cl | H | 3 | —NH—(CH$_2$)$_2$—SO$_2$—NH$_2$ | 2HCl | 191–193 |
| 11 | 2-OCH$_3$, 5-Cl | H | 3 | —NH—(CH$_2$)$_2$—SO$_2$—NH$_2$ | base | 165.5–167.5 |
| 12 | 2-OCH$_3$, 5-Cl | H | 3 | —NH—(CH$_2$)$_2$—SO$_2$—CH$_3$ | base | 104.5–106.5 |
| 13 | 3-Cl | H | 3 | —NH—(CH$_2$)$_2$—NH—SO$_2$—CH$_3$ | 2HCl | 174–176 |
| 14 | 2-OCH$_3$, 5-Cl | H | 3 | —NH—(CH$_2$)$_2$—NH—SO$_2$—CH$_3$ | base, ½H$_2$O | 127–129 |
| 15 | 2-OCH$_3$, 5-Cl | H | 3 | —NH—CH$_2$—CO—NH$_2$ | HCl, ½H$_2$O | 195–197 |
| 16 | 2-OCH$_3$, 5-Cl | H | 3 | —NH—CH$_2$—CO—N(CH$_3$)$_2$ | base | 153.5–154.5 |
| 17 | 2-OCH$_3$, 5-Cl | H | 3 | —NH—CH$_2$—CO—NH—(CH$_2$)$_2$—CH$_3$ | base | 143.5–145.5 |
| 18 | 2-OCH$_3$, 5-Cl | H | 3 | —NH—CH$_2$—CO—NH—(CH$_2$)$_5$—CH$_3$ | base | 122–124 |
| 19 | 3-Cl | H | 3 | —NH—(CH$_2$)$_2$—C$_6$H$_3$(OCH$_3$)$_2$ | 2HCl | 172.5–174 |
| 20 | 2-OCH$_3$, 5-Cl | H | 3 | —NH—(CH$_2$)$_2$—C$_6$H$_3$(OCH$_3$)$_2$ | 2HCl | 182–185 |
| 21 | 2-OCH$_3$, 5-Cl | H | 3 | —NH—(CH$_2$)$_2$—C$_6$H$_4$—SO$_2$—NH$_2$ | 2HCl | 204–205 |
| 22 | 2-OCH$_3$, 5-Cl | H | 2 | —NH—(CH$_2$)$_3$—NH—(pyrimidinone) | base | 227–230 |
| 23 | 2-OCH$_3$, 5-Cl | H | 3 | —NH—(CH$_2$)$_2$—NH—(pyrimidinone) | base | 118–120 |
| 24 | 2-OCH$_3$, 5-F | H | 3 | —NH—(CH$_2$)$_2$—NH—(pyrimidinone) | base | 99–101 |
| 25 | 2-OCH$_3$, 5-Cl | H | 3 | —NH—(CH$_2$)$_2$—NH—(pyrimidinone) | base, ½H$_2$O | 229–232 |
| 26 | 2-OCH$_3$, 5-F | H | 3 | —NH—(CH$_2$)$_2$—NH—(pyrimidinone) | base | 218.5–221 |

TABLE-continued (I)

[Structure: X-phenyl-N-piperazine-(CH2)n-N(R)-pyrimidine-C(O)-NR1R2]

| N° | X | R | n | —NR₁R₂ | Salt or base | M.p. (°C.) |
|---|---|---|---|---|---|---|
| 27 | 2-OCH₃, 5-Cl | H | 3 | —NH—(CH₂)₃—NH-[4-oxo-pyrimidin-2-yl] | base | 101–103 |
| 28 | 2-OCH₃, 5-F | H | 3 | —NH—(CH₂)₃—NH-[4-oxo-pyrimidin-2-yl] | base | 94–97 |
| 29 | 2-OCH₃, 5-Cl | H | 3 | —NH—(CH₂)₃—NH-[2-oxo-pyrimidin-4-yl] | base, ½H₂O | 218–219.5 |
| 30 | 2-OCH₃, 5-F | H | 3 | —NH—(CH₂)₃—NH-[2-oxo-pyrimidin-4-yl] | base | 219–221 |
| 31 | 3-Cl | H | 2 | —NH—(CH₂)₂—NH-[4-oxo-pyrimidin-2-yl] | base | 112–116 |
| 32 | 2-OCH₃, 5-Cl | H | 2 | —NH—(CH₂)₂—NH-[4-oxo-pyrimidin-2-yl] | base | 123–126 |
| 33 | 3-Cl | H | 2 | —NH—(CH₂)₂—NH-[2-oxo-pyrimidin-4-yl] | base | 242–245 |
| 34 | 3-Cl | H | 2 | —NH—(CH₂)₃—NH-[4-oxo-pyrimidin-2-yl] | base | 111–115 |
| 35 | 2-OCH₃, 5-Cl | H | 2 | —NH—(CH₂)₃—NH-[4-oxo-pyrimidin-2-yl] | base, ½H₂O | 100–102 |
| 36 | 3-Cl | H | 2 | —NH—(CH₂)₃—NH-[2-oxo-pyrimidin-4-yl] | base | 197–200 |

TABLE-continued

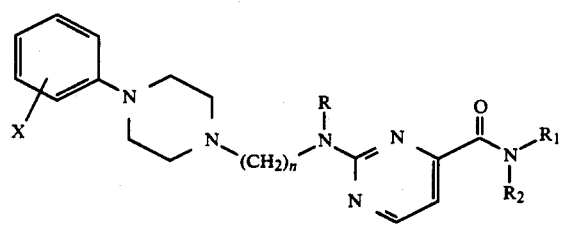

(I)

| N° | X | R | n | —NR₁R₂ | Salt or base | M.p. (°C.) |
|---|---|---|---|---|---|---|
| 37 | 2-OCH₃, 5-Cl | H | 2 | —NH—(CH₂)₄—NH— [2-amino-pyrimidin-4(3H)-one] | base | 98–100 |
| 38 | 2-OCH₃, 5-Cl | H | 3 | —NH—CH₂—C(CH₃)₂—CH₂—NH— [2-amino-pyrimidin-4(3H)-one] | base | 116–120 |
| 39 | 2-OCH₃, 5-Cl | H | 2 | —NH—CH₂—C(CH₃)₂—CH₂—NH— [2-amino-pyrimidin-4(3H)-one] | base | 117–121 |
| 40 | 2-OCH₃, 5-OCH₃ | H | 2 | —NH—(CH₂)₃—NH— [2-amino-pyrimidin-4(3H)-one] | base | 95–97 |
| 41 | 2-OCH₃, 5-OCH₃ | H | 3 | —NH—(CH₂)₂—NH— [2-amino-pyrimidin-4(3H)-one] | base | 105–110 |
| 42 | 2-OCH₃, 5-OCH₃ | H | 2 | —NH—(CH₂)₂—NH— [2-amino-pyrimidin-4(3H)-one] | base | 103–107 |
| 43 | 2-OCH₃, 5-F | H | 2 | —NH—(CH₂)₃—NH— [2-amino-pyrimidin-4(3H)-one] | base | 120–122 |
| 44 | 2-OCH₃, 5-Cl | H | 2 | —NH—CH₂—C(CH₃)₂—CH₂—NH— [4-amino-pyrimidin-2(1H)-one] | base | 125–128 |
| 45 | 2-OCH₃, 5-F | H | 2 | —NH—CH₂—C(CH₃)₂—CH₂—NH— [4-amino-pyrimidin-2(1H)-one] | base | 184–187 |

TABLE-continued

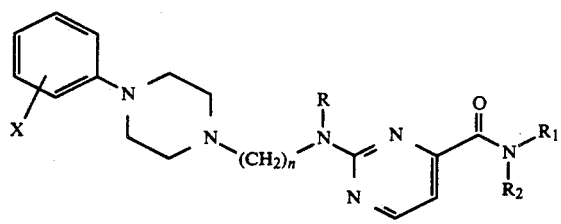

(I)

| N° | X | R | n | —NR₁R₂ | Salt or base | M.p. (°C.) |
|---|---|---|---|---|---|---|
| 46 | 2-OCH₃, 5-Cl | H | 3 | —NH—CH₂—[4-piperidinyl-N(2-pyrimidinyl-6-one)] | ½C₂H₂O₄, ½H₂O | 138–142 |
| 47 | 2-OCH₃, 5-Cl | H | 3 | —NH—[4-piperidinyl-N(2-pyrimidinyl-6-one)] | C₂H₂O₄, H₂O | 136–140 |
| 48 | 2-OCH₃, 5-Cl | H | 2 | —NH—CH₂—[4-piperidinyl-N(2-pyrimidinyl-6-one)] | C₂H₂O₄, ½H₂O | 155–160 |
| 49 | 2-OCH₃, 5-Cl | H | 2 | —NH—[4-piperidinyl-N(2-pyrimidinyl-6-one)] | base | 112–116 |
| 50 | 2-OCH₃, 5-Cl | H | 2 | —NH—CH₂—[3-piperidinyl-N(2-pyrimidinyl-6-one)] | base | 104–108 |
| 51 | 2-OCH₃, 5-Cl | H | 3 | —NH—(CH₂)₂—NH—CO—(pyridyl) | base | 124–127 |
| 52 | 2-OCH₃, 5-Cl | H | 3 | —NH—(CH₂)₂—NH—CO—(5-Cl, 4-NH₂, 2-OCH₃-phenyl) | C₂H₂O₄, ½H₂O | 153–157 |
| 53 | 2-OCH₃, 5-Cl | H | 3 | —NH—(CH₂)₂—NH—CO—(4-OCH₃, 2-OCH₃-phenyl) | C₂H₂O₄ | 113–117 |

TABLE-continued
(I)
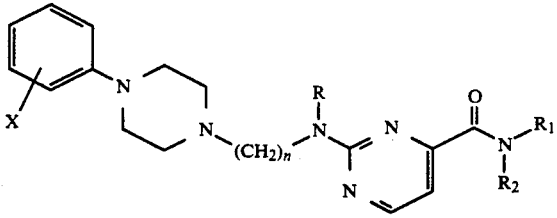
| N° | X | R | n | —NR₁R₂ | Salt or base | M.p. (°C.) |
|---|---|---|---|---|---|---|
| 54 | 2-OCH₃, 5-Cl | H | 3 | 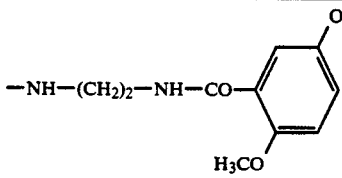 | C₂H₂O₄ | 106–110 |
| 55 | 2-OCH₃, 5-Cl | H | 3 | 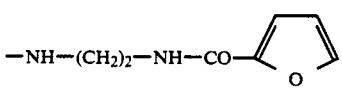 | C₂H₂O₄ | 126–130 |
| 56 | 2-OCH₃, 5-Cl | H | 3 | 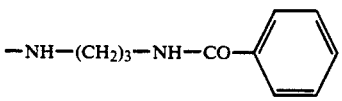 | ½C₂H₂O₄ | 172–175 |
| 57 | 2-OCH₃, 5-Cl | H | 3 | 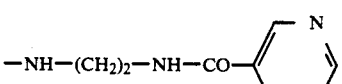 | C₂H₂O₄ | 118–122 |
| 58 | 2-OCH₃, 5-Cl | H | 3 | 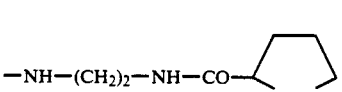 | C₂H₂O₄ | 151–155 |
| 59 | 2-OCH₃, 5-Cl | H | 2 | 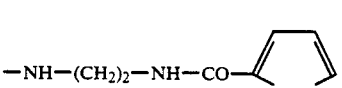 | C₂H₂O₄ | 128–132 |
| 60 | 3-Cl | H | 3 | —N(CH₃)₂ | 2HCl | 194–198 |
| 61 | 2-OCH₃, 5-Cl | H | 3 | —N(CH₃)₂ | HCl | 196–199 |
| 62 | 3-Cl | H | 3 |  | 2HCl | 194–195 |
| 63 | 2-OCH₃, 5-Cl | H | 3 |  | 2HCl | 194–197 |
| 64 | 3-Cl | H | 3 |  | 2HCl | 192–196 |
| 65 | 2-OCH₃, 5-Cl | H | 3 |  | 2HCl | 166–169 |
| 66 | 2-OCH₃, 5-Cl | H | 3 |  | base | 98.5–99.5 |

TABLE-continued
(I)
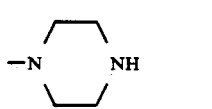
| N° | X | R | n | —NR₁R₂ | Salt or base | M.p. (°C.) |
|---|---|---|---|---|---|---|
| 67 | 2-OCH₃, 5-Cl | H | 3 | 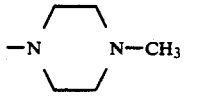 | 2HCl | 189–191 |
| 68 | 3-Cl | H | 3 | 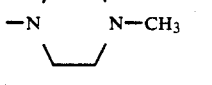 | 2HCl, H₂O | 162–165 |
| 69 | 2-OCH₃, 5-Cl | H | 3 | 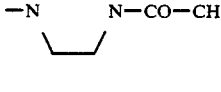 | 2HCl, ½H₂O | 253–256 |
| 70 | 3-Cl | H | 3 | 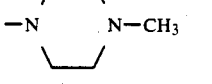 | HCl | 179–181 |
| 71 | 3-Cl | H | 2 | 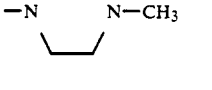 | 2HCl | 254–257 |
| 72 | 2-OCH₃, 5-Cl | H | 2 | 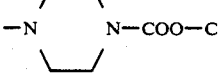 | 2HCl | 255–257 |
| 73 | 2-OCH₃, 5-Cl | H | 3 | 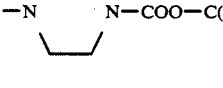 | HCl | 206.5–207.5 |
| 74 | 3-Cl | H | 3 | 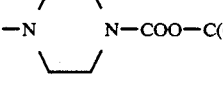 | HCl | 207–209 |
| 75 | 2-OCH₃, 5-Cl | H | 2 | 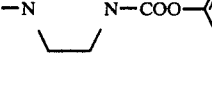 | HCl | 210–211.5 |
| 76 | 2-OCH₃, 5-Cl | H | 3 | 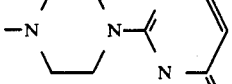 | HCl | 162–165 |
| 77 | 2-OCH₃, 5-Cl | H | 3 |  | base | 107–110 |

TABLE-continued
(I)
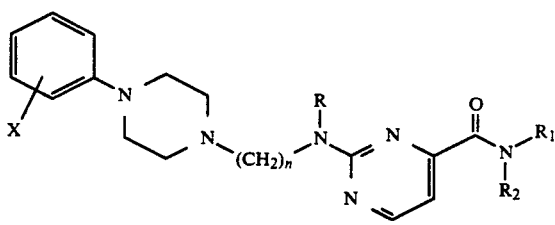
| N° | X | R | n | —NR₁R₂ | Salt or base | M.p. (°C.) |
|---|---|---|---|---|---|---|
| 78 | 2-OCH₃, 5-Cl | H | 2 | 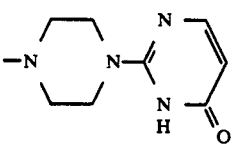 | base | 110–113 |
| 79 | 2-OCH₃, 5-Cl | H | 2 | 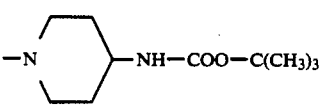 | HCl | 194–197 |
| 80 | 2-OCH₃, 5-Cl | H | 2 | 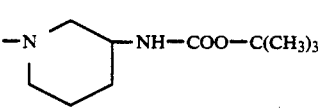 | base | 72–76 |
| 81 | 2-OCH₃, 5-Cl | H | 2 | 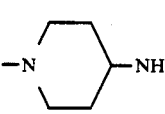 | base | amorphous solid |
| 82 | 2-OCH₃, 5-Cl | H | 2 | 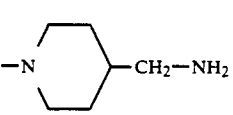 | base | amorphous solid |
| 83 | 2-OCH₃, 5-Cl | H | 2 | 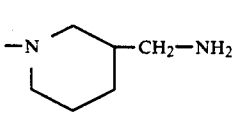 | base | amorphous solid |
| 84 | 2-OCH₃, 5-Cl | H | 3 | 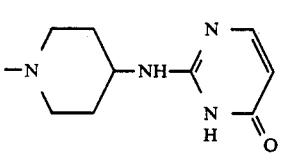 | base | 128–131 |
| 85 | 2-OCH₃, 5-Cl | H | 2 | 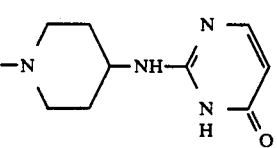 | base | 114–117 |
| 86 | 2-OCH₃, 5-Cl | H | 3 | 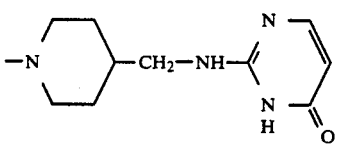 | C₂H₂O₄, H₂O | 150–154 |
| 87 | 2-OCH₃, 5-Cl | H | 2 | 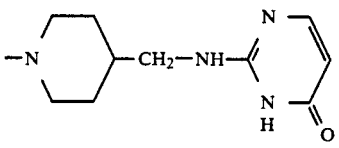 | C₂H₂O₄ | 147–150 |

TABLE-continued

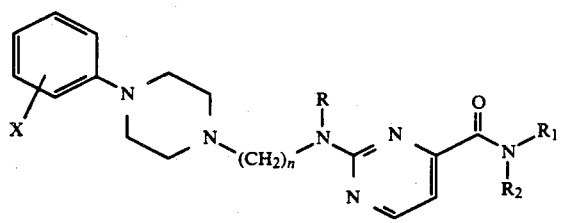
(I)

| N° | X | R | n | —NR₁R₂ | Salt or base | M.p. (°C.) |
|---|---|---|---|---|---|---|
| 88 | 2-OCH$_3$, 5-Cl | H | 2 | —N⟨piperidine⟩—CH$_2$—NH—(pyrimidinone) | base | 105–108 |
| 89 | 2-OCH$_3$, 5-Cl | H | 3 | —N(CH$_3$)—(CH$_2$)$_3$—N(CH$_3$)—(pyrimidinone) | base | 87–92 |
| 90 | 3-Cl | CH$_3$ | 3 | —N(CH$_3$)$_2$ | HCl | 163–166 |

Legend
In the column "Salt or base", HCl denotes a hydrochloride, 2HCl denotes a dihydrochloride, C$_2$H$_2$O$_4$ denotes a hydrogen oxalate, ½C$_2$H$_2$O$_4$ denotes a neutral oxalate, H$_2$O denotes a hydrated compound and ½H$_2$O denotes a hemihydrated compound.

The compounds of the invention were subjected to studies of their antagonist activity with respect to $\alpha_1$-adrenoceptors in the lower urinary tract.

Their in vitro activity was studied on isolated rabbit urethra.

Rings of adult rabbit urethra are prepared according to the method of Ueda et al., Eur. J. Pharmacol., (1984), 103, 249–254, and then, after sensitisation to nonadrenaline, the curve of concentration-response to phenylephrine is determined in the absence and presence of the test compound The potency of the $\alpha_1$-adrenergic antagonism of each compound is evaluated by calculating the pA$_2$, the antilogarithm of the molar concentration of antagonist in the presence of which the agonist concentration must be doubled in order to generate the same effect as in its absence.

The pA$_2$ values of the compounds are of the order of 5.5 to 9.

The in vivo activity of the compounds of the invention was studied in respect of their effect on urethral hypertonia generated by stimulation of the sympathetic fibres of the hypogastric nerve in anaesthetised cats.

Adult male cats are anaesthetised with pentobarbitone sodium, and prepared according to the method of Theobald, J. Auton. Pharmac., (1983), 3, 235–239, so as to obtain a urethral hypertonia by stimulation of the sympathetic fibres of the hypogastric nerve. The contractile responses of the urethra to electrical stimulation of the hypogastric nerve are noted before and after intravenous administration of the test compounds at cumulative doses from 1 to 1,000 μg/kg.

The potency of the $\alpha_1$-adrenergic antagonism of each compound is evaluated by calculating the ID$_{50}$, the dose which inhibits urethral hypertonia by 50%.

The ID$_{50}$ values of the compounds of the invention are of the order of 0.01 to 1 mg/kg.

The results of the tests show that the compounds of the invention show in vitro an antagonist activity with respect to the $\alpha_1$-adrenoceptors of the smooth muscles of the lower urinary tract (urethra) when the muscles are stimulated by an $\alpha_1$-adrenergic agonist (phenylephrine). In vivo, they inhibit urethral hypertonia generated by stimulation of the sympathetic nervous system.

The compounds of the invention can hence be used for the symptomatic treatment of diseases and conditions involving a hyperactivity of the $\alpha$-adrenergic system in the lower urinary tract, and in particular for the treatment of benign hypertrophy of the prostate, dysuria and pollakiuria.

Thus, the invention includes a pharmaceutical composition comprising a pharmaceutically acceptable excipient and, as an active ingredient, a compound of the invention.

The invention further includes a method of treatment of disorders involving $\alpha_1$-adrenergic receptors, comprising administering to a patient a compound of the invention.

For this purpose, they may be presented in all forms suited to enteral or parenteral administration, in combination with pharmaceutical excipients, for example in the form of tablets, dragees, capsules including hard gelatin capsules, solutions or suspensions to be taken by mouth or injected, and suppositories, their content being such as to permit a daily dose of 0.5 to 500 mg of active substance.

We claim:
1. A compound which is a 2-aminopyrimidine-4-carboxamide derivative represented by formula (I)

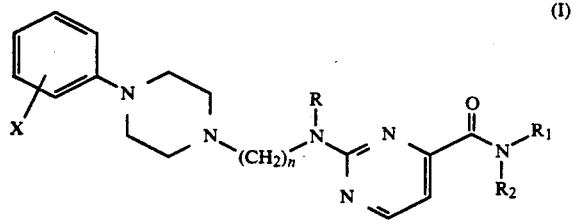

(I)

in which
n represents 2 or 3,
X represents a substituent selected from the group consisting of hydrogen, fluorine, chlorine and methoxy, with the proviso that more than one substituent X may be present in which case each X may be the same or different,
R represents hydrogen or methyl,
$R_1$ represents hydrogen or methyl,
$R_2$ represents a substituent selected from the group consisting of
$C_1$-$C_6$ alkyl
$C_2$-$C_3$ hydroxyalkyl,
(hydroxy)(methoxy)($C_2$-$C_3$ alkyl),
dimethoxy($C_2$-$C_3$ alkyl),
2-(aminosulphonyl)ethyl,
2-(methylsulphonyl)ethyl,
2-(methylsulphonylamino)ethyl,
a group of formula —$CH_2$—CO—$NY_1Y_2$ in which $Y_1$ and $Y_2$, which may be the same or different, each represent hydrogen or $C_1$-$C_6$ alkyl,
a group of formula —$(CH_2)_2$—Ar in which Ar represents phenyl, optionally substituted by one or more methoxy or aminosulphonyl groups,
a group of formula

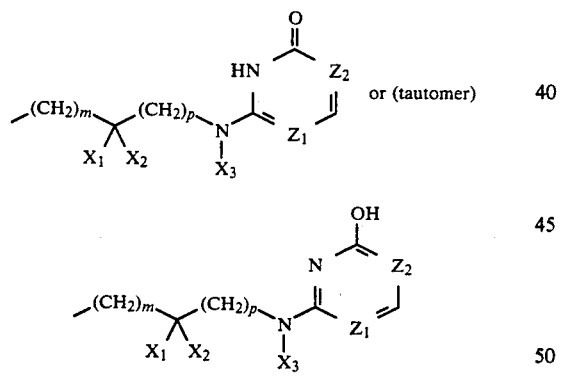

in which m represents 0 or 1, p represents 1 or 2, one of $Z_1$ and $Z_2$ represents —CH— and the other represents a nitrogen atom, and either $X_1$, $X_2$ and $X_3$ each represent hydrogen or $X_1$ and $X_2$ each represent methyl and $X_3$ represents hydrogen or $X_1$ represents hydrogen and $X_2$ and $X_3$ together form a chain of formula —$(CH_2)_{4-p}$ in which p is as defined above, and
a group of formula

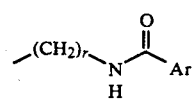

in which r represents 2 or 3 and Ar represents a group selected from phenyl optionally substituted by one or more substituents selected from chloro, methoxy and amino groups, 2-furanyl, 2-tetrahydrofuranyl and 3-pyridinyl, or $R_1$ and $R_2$ form, together with the nitrogen atom to which they are attached, a group selected from a group of formula

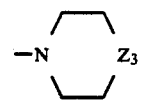

in which $Z_3$ represents a group selected from oxygen, sulphur, sulphonyl and a group of formula N-$R_4$ in which $R_4$ represents a substituent selected from hydrogen, methyl, acetyl, tert-butyloxycarbonyl, phenyloxycarbonyl and a group of formula

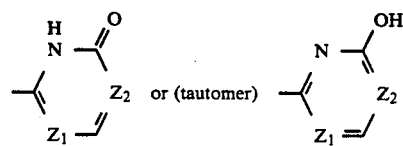

in which $Z_1$ and $Z_2$ are as defined above, and a group of formula

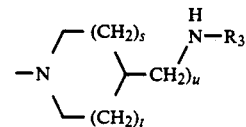

in which either s represents 0 and t represents 2, or both s and t represent 1, u represents 0 or 1 and $R_3$ represents a group selected from hydrogen, tert-butyloxycarbonyl, benzyloxycarbonyl and a group of formula

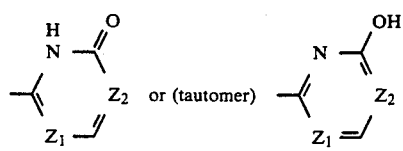

in which $Z_1$ and $Z_2$ are as defined above; or a pharmaceutically acceptable acid addition salt thereof.

2. A compound according to claim 1 in which one or two substituents X are present.

3. A compound according to claim 1 in which one substituent X is present and which is at the 3-position.

4. A compound according to claim 2 in which two substituents X are present at the 2- and 5-positions.

5. A compound according to claim 4 in which methoxy is at the 2-position and chloro is at the 5-position.

6. A pharmaceutical composition comprising a pharmaceutically acceptable carrier and an effective amount of a compound as claimed in claim 1 for treating disorders involving hyperactivity of the α-adrenergic system in the lower urinary tract.

7. A method of treatment of disorders involving hyperactivity of the $α_1$-adrenergic system in the lower urinary tract, comprising administering to a patient an effective amount of a compound as claimed in claim 1.

* * * * *